(12) United States Patent
Kim et al.

(10) Patent No.: US 8,901,081 B2
(45) Date of Patent: Dec. 2, 2014

(54) USES OF GRS PROTEINS OR FRAGMENTS THEREOF

(75) Inventors: Sunghoon Kim, Seoul (KR); Min Chul Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/123,522

(22) PCT Filed: Oct. 12, 2009

(86) PCT No.: PCT/KR2009/005829
§ 371 (c)(1),
(2), (4) Date: Jun. 24, 2011

(87) PCT Pub. No.: WO2010/041913
PCT Pub. Date: Apr. 15, 2010

(65) Prior Publication Data
US 2011/0256119 A1    Oct. 20, 2011

(30) Foreign Application Priority Data

Oct. 10, 2008    (KR) .................. 10-2008-0099784

(51) Int. Cl.
| | |
|---|---|
| *C07K 1/00* | (2006.01) |
| *A61K 38/24* | (2006.01) |
| *A61K 38/27* | (2006.01) |
| *A61K 38/00* | (2006.01) |
| *A61K 38/53* | (2006.01) |

(52) U.S. Cl.
CPC ......... *C12Y 601/01014* (2013.01); *A61K 38/53* (2013.01)
USPC ............ 514/18.9; 530/350; 530/399; 514/1.1

(58) Field of Classification Search
None
See application file for complete search history.

(56) References Cited

U.S. PATENT DOCUMENTS 6,506,607 B1 * 1/2003 Shyjan ............................ 436/94
2010/0028352 A1 * 2/2010 Greene et al. ............... 424/139.1

OTHER PUBLICATIONS

Gillet et al., The Development of Gene Therapy: From Monogenic Recessive Disorders to Complex Diseases Such as Cancer; Methods in Mol Biol, vol. 542, pp. 5-54, 2009.*

* cited by examiner

*Primary Examiner* — Jennifer Dunston
*Assistant Examiner* — Addison D Ault
(74) *Attorney, Agent, or Firm* — Edwards Wildman Palmer LLP; Kongsik Kim; Richard B. Emmons

(57) ABSTRACT

The present invention is related to a anticancer composition comprising full length GRS protein or a fragment thereof, a nucleic acid encoding the GRS protein or a fragment thereof. Since the GRS proteins or fragments thereof have activity to induce apoptosis of cancer cell specifically, a composition comprising the GRS proteins or fragments thereof or a nucleic acid encoding thereof may be useful to treatment of cancer.

2 Claims, 10 Drawing Sheets

Cytochrome C Release

SEQUENCE LISTING

```
<160> NUMBER OF SEQ ID NOS: 7

<210> SEQ ID NO 1
<211> LENGTH: 685
<212> TYPE: PRT
<213> ORGANISM: Homo sapiens
<220> FEATURE:
<221> NAME/KEY: PEPTIDE
<222> LOCATION: (1)..(685)
<223> OTHER INFORMATION: full length of GRS

<400> SEQUENCE: 1

Met Asp Gly Ala Gly Ala Glu Glu Val Leu Ala Pro Leu Arg Leu Ala
 1               5                   10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Asp Ile
        50                  55                  60

Val Asp Arg Ala Lys Met Glu Asp Thr Leu Lys Arg Arg Phe Phe Tyr
 65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160
```

```
Asp His Leu Leu Lys Ala His Leu Gln Lys Leu Met Ser Asp Lys Lys
            165                 170                 175
Cys Ser Val Glu Lys Lys Ser Glu Met Glu Ser Val Leu Ala Gln Leu
            180                 185                 190
Asp Asn Tyr Gly Gln Gln Glu Leu Ala Asp Leu Phe Val Asn Tyr Asn
            195                 200                 205
Val Lys Ser Pro Ile Thr Gly Asn Asp Leu Ser Pro Pro Val Ser Phe
            210                 215                 220
Asn Leu Met Phe Lys Thr Phe Ile Gly Pro Gly Asn Met Pro Gly
225                 230                 235                 240
Tyr Leu Arg Pro Glu Thr Ala Gln Gly Ile Phe Leu Asn Phe Lys Arg
            245                 250                 255
Leu Leu Glu Phe Asn Gln Gly Lys Leu Pro Phe Ala Ala Ala Gln Ile
            260                 265                 270
Gly Asn Ser Phe Arg Asn Glu Ile Ser Pro Arg Ser Gly Leu Ile Arg
            275                 280                 285
Val Arg Glu Phe Thr Met Ala Glu Ile Glu His Phe Val Asp Pro Ser
            290                 295                 300
Glu Lys Asp His Pro Lys Phe Gln Asn Val Ala Asp Leu His Leu Tyr
305                 310                 315                 320
Leu Tyr Ser Ala Lys Ala Gln Val Ser Gly Gln Ser Ala Arg Lys Met
            325                 330                 335
Arg Leu Gly Asp Ala Val Glu Gln Gly Val Ile Asn Asn Thr Val Leu
            340                 345                 350
Gly Tyr Phe Ile Gly Arg Ile Tyr Leu Tyr Leu Thr Lys Val Gly Ile
            355                 360                 365
Ser Pro Asp Lys Leu Arg Phe Arg Gln His Met Glu Asn Glu Met Ala
            370                 375                 380
His Tyr Ala Cys Asp Cys Trp Asp Ala Glu Ser Lys Thr Ser Tyr Gly
385                 390                 395                 400
Trp Ile Glu Ile Val Gly Cys Ala Asp Arg Ser Cys Tyr Asp Leu Ser
            405                 410                 415
Cys His Ala Arg Ala Thr Lys Val Pro Leu Val Ala Glu Lys Pro Leu
            420                 425                 430
Lys Glu Pro Lys Thr Val Asn Val Val Gln Phe Glu Pro Ser Lys Gly
            435                 440                 445
Ala Ile Gly Lys Ala Tyr Lys Lys Asp Ala Lys Leu Val Met Glu Tyr
            450                 455                 460
Leu Ala Ile Cys Asp Glu Cys Tyr Ile Thr Glu Ile Glu Met Leu Leu
465                 470                 475                 480
Asn Glu Lys Gly Glu Phe Thr Ile Glu Thr Glu Gly Lys Thr Phe Gln
            485                 490                 495
Leu Thr Lys Asp Met Ile Asn Val Lys Arg Phe Gln Lys Thr Leu Tyr
            500                 505                 510
Val Glu Glu Val Val Pro Asn Val Ile Glu Pro Ser Phe Gly Leu Gly
            515                 520                 525
Arg Ile Met Tyr Thr Val Phe Glu His Thr Phe His Val Arg Glu Gly
            530                 535                 540
Asp Glu Gln Arg Thr Phe Phe Ser Phe Pro Ala Val Val Ala Pro Phe
545                 550                 555                 560
Lys Cys Ser Val Leu Pro Leu Ser Gln Asn Gln Glu Phe Met Pro Phe
            565                 570                 575
```

| Val | Lys | Glu | Leu | Ser | Glu | Ala | Leu | Thr | Arg | His | Gly | Val | Ser | His | Lys |
|-----|-----|-----|-----|-----|-----|-----|-----|-----|-----|-----|-----|-----|-----|-----|-----|
|     |     |     |     | 580 |     |     |     |     | 585 |     |     |     |     | 590 |     |

| Val | Asp | Asp | Ser | Ser | Gly | Ser | Ile | Gly | Arg | Arg | Tyr | Ala | Arg | Thr | Asp |
|-----|-----|-----|-----|-----|-----|-----|-----|-----|-----|-----|-----|-----|-----|-----|-----|
|     |     |     | 595 |     |     |     |     | 600 |     |     |     |     | 605 |     |     |

| Glu | Ile | Gly | Val | Ala | Phe | Gly | Val | Thr | Ile | Asp | Phe | Asp | Thr | Val | Asn |
|-----|-----|-----|-----|-----|-----|-----|-----|-----|-----|-----|-----|-----|-----|-----|-----|
|     | 610 |     |     |     |     | 615 |     |     |     |     | 620 |     |     |     |     |

| Lys | Thr | Pro | His | Thr | Ala | Thr | Leu | Arg | Asp | Arg | Asp | Ser | Met | Arg | Gln |
|-----|-----|-----|-----|-----|-----|-----|-----|-----|-----|-----|-----|-----|-----|-----|-----|
| 625 |     |     |     |     | 630 |     |     |     |     | 635 |     |     |     |     | 640 |

| Ile | Arg | Ala | Glu | Ile | Ser | Glu | Leu | Pro | Ser | Ile | Val | Gln | Asp | Leu | Ala |
|-----|-----|-----|-----|-----|-----|-----|-----|-----|-----|-----|-----|-----|-----|-----|-----|
|     |     |     |     |     | 645 |     |     |     |     | 650 |     |     |     |     | 655 |

| Asn | Gly | Asn | Ile | Thr | Trp | Ala | Asp | Val | Glu | Ala | Arg | Tyr | Pro | Leu | Phe |
|-----|-----|-----|-----|-----|-----|-----|-----|-----|-----|-----|-----|-----|-----|-----|-----|
|     |     |     | 660 |     |     |     |     | 665 |     |     |     |     | 670 |     |     |

| Glu | Gly | Gln | Glu | Thr | Gly | Lys | Lys | Glu | Thr | Ile | Glu | Glu |
|-----|-----|-----|-----|-----|-----|-----|-----|-----|-----|-----|-----|-----|
|     | 675 |     |     |     |     | 680 |     |     |     |     | 685 |     |

<210> SEQ ID NO 2
<211> LENGTH: 2058
<212> TYPE: DNA
<213> ORGANISM: Homo sapiens

<400> SEQUENCE: 2

| atggacggcg cgggggctga ggaggtgctg gctcctctga ggctagcagt gcgccagcag | 60 |
| ggagatcttg tgcgaaaact caaagaagat aaagcacccc aagtagacgt agacaaagca | 120 |
| gtggctgagc tcaaagcccg caagagggtt ctggaagcaa aggagctggc gttacagccc | 180 |
| aaagatgata ttgtagaccg agcaaaaatg aagataccc tgaagaggag gtttttctat | 240 |
| gatcaagctt ttgctatttta tggaggtgtt agtggtctgt atgactttgg gccagttggc | 300 |
| tgtgctttga gaacaatat tattcagacc tggaggcagc actttatcca agaggaacag | 360 |
| atcctggaga tcgattgcac catgctcacc cctgagccag tttttaaagac ctctggccat | 420 |
| gtagacaaat ttgctgactt catggtgaaa gacgtaaaaa atggagaatg ttttcgtgct | 480 |
| gaccatctat taaaagctca tttacagaaa ttgatgtctg ataagaagtg ttctgtcgaa | 540 |
| aagaaatcag aaatggaaag tgttttggcc cagcttgata ctatggaca gcaagaactt | 600 |
| gcggatcttt ttgtgaacta taatgtaaaa tctcccatta ctggaaatga tctatcccct | 660 |
| ccagtgtctt ttaacttaat gttcaagact tcattgggc ctggaggaaa catgcctggg | 720 |
| tacttgagac agaaactgc acaggggatt ttcttgaatt tcaaacgact tttggagttc | 780 |
| aaccaaggaa agttgccttt gctgctgcc cagattggaa attcttttag aaatgagatc | 840 |
| tccctcgat ctggactgat cagagtcaga gaattcacaa tggcagaaat tgagcacttt | 900 |
| gtagatccca gtgagaaaga ccaccccaag ttccagaatg tggcagacct tcacctttat | 960 |
| ttgtattcag caaagccca ggtcagcgga cagtccgctc ggaaaatgcg cctgggagat | 1020 |
| gctgttgaac agggtgtgat taataacaca gtattaggct atttcattgg ccgcatctac | 1080 |
| ctctacctca cgaaggttgg aatatctcca gataaactcc gcttccggca gcacatggag | 1140 |
| aatgagatgg cccattatgc ctgtgactgt tgggatgcag aatccaaaac atcctacggt | 1200 |
| tggattgaga ttgttggatg tgctgatcgt tcctgttatg acctctcctg tcatgcacga | 1260 |
| gccaccaaag tcccacttgt agctgagaaa cctctgaaag acccaaaac agtcaatgtt | 1320 |
| gttcagtttg aacccagtaa gggagcaatt ggtaaggcat ataagaagga tgcaaaactg | 1380 |
| gtgatggagt atcttgccat ttgtgatgag tgctacatta cagaaattga atgctgctg | 1440 |
| aatgagaaag gggaattcac aattgaaact gaagggaaaa catttcagtt aacaaaagac | 1500 |

```
atgatcaatg tgaagagatt ccagaaaaca ctatatgtgg aagaagttgt tccgaatgta      1560
attgaaccct tccttcggcct gggtaggatc atgtatacgg tatttgaaca tacattccat      1620
gtacgagaag gagatgaaca gagaacattc ttcagtttcc ctgctgtagt tgctccattc      1680
aaatgttccg tcctcccact gagccaaaac caggagttca tgccatttgt caaggaatta      1740
tcggaagccc tgaccaggca tggagtatct cacaaagtag acgattcctc tgggtcaatc      1800
ggaaggcgct atgccaggac tgatgagatt ggcgtggctt ttggtgtcac cattgacttt      1860
gacacagtga acaagacccc ccacactgca actctgaggg accgtgactc aatgcggcag      1920 ataagcagc agatctctga gctgcccagc atagtccaag acctagccaa tgcaacatc       1980 acatgggctg atgtggaggc caggtatcct ctgtttgaag gcaagagac tggtaaaaaa      2040 gagacaatcg aggaatga                                                    2058
```

<210> SEQ ID NO 3
<211> LENGTH: 136
<212> TYPE: PRT
<213> ORGANISM: Homo sapiens
<220> FEATURE:
<221> NAME/KEY: DOMAIN
<222> LOCATION: (1)..(136)
<223> OTHER INFORMATION: Fragment 1 (1-136aa)

<400> SEQUENCE: 3

Met Asp Gly Ala Gly Ala Glu Glu Val Leu Ala Pro Leu Arg Leu Ala
 1               5                  10                  15

Val Arg Gln Gln Gly Asp Leu Val Arg Lys Leu Lys Glu Asp Lys Ala
             20                  25                  30

Pro Gln Val Asp Val Asp Lys Ala Val Ala Glu Leu Lys Ala Arg Lys
         35                  40                  45

Arg Val Leu Glu Ala Lys Glu Leu Ala Leu Gln Pro Lys Asp Asp Ile
     50                  55                  60

Val Asp Arg Ala Lys Met Glu Asp Thr Leu Lys Arg Arg Phe Phe Tyr
 65                  70                  75                  80

Asp Gln Ala Phe Ala Ile Tyr Gly Gly Val Ser Gly Leu Tyr Asp Phe
                 85                  90                  95

Gly Pro Val Gly Cys Ala Leu Lys Asn Asn Ile Ile Gln Thr Trp Arg
            100                 105                 110

Gln His Phe Ile Gln Glu Gln Ile Leu Glu Ile Asp Cys Thr Met
        115                 120                 125

Leu Thr Pro Glu Pro Val Leu Lys
    130                 135

<210> SEQ ID NO 4
<211> LENGTH: 174
<212> TYPE: PRT
<213> ORGANISM: Homo sapiens
<220> FEATURE:
<221> NAME/KEY: DOMAIN
<222> LOCATION: (1)..(174)
<223> OTHER INFORMATION: Fragment 2 (137-310aa)

<400> SEQUENCE: 4

Thr Ser Gly His Val Asp Lys Phe Ala Asp Phe Met Val Lys Asp Val
 1               5                  10                  15

Lys Asn Gly Glu Cys Phe Arg Ala Asp His Leu Leu Lys Ala His Leu
             20                  25                  30

Gln Lys Leu Met Ser Asp Lys Lys Cys Ser Val Glu Lys Lys Ser Glu
         35                  40                  45

```
Met Glu Ser Val Leu Ala Gln Leu Asp Asn Tyr Gly Gln Gln Glu Leu
            50                  55                  60

Ala Asp Leu Phe Val Asn Tyr Asn Val Lys Ser Pro Ile Thr Gly Asn
 65                  70                  75                  80

Asp Leu Ser Pro Pro Val Ser Phe Asn Leu Met Phe Lys Thr Phe Ile
                85                  90                  95

Gly Pro Gly Gly Asn Met Pro Gly Tyr Leu Arg Pro Glu Thr Ala Gln
            100                 105                 110

Gly Ile Phe Leu Asn Phe Lys Arg Leu Leu Glu Phe Asn Gln Gly Lys
            115                 120                 125

Leu Pro Phe Ala Ala Ala Gln Ile Gly Asn Ser Phe Arg Asn Glu Ile
130                 135                 140

Ser Pro Arg Ser Gly Leu Ile Arg Val Arg Glu Phe Thr Met Ala Glu
145                 150                 155                 160

Ile Glu His Phe Val Asp Pro Ser Glu Lys Asp His Pro Lys
                165                 170
```

<210> SEQ ID NO 5
<211> LENGTH: 200
<212> TYPE: PRT
<213> ORGANISM: Homo sapiens
<220> FEATURE:
<221> NAME/KEY: DOMAIN
<222> LOCATION: (1)..(200)
<223> OTHER INFORMATION: Fragment 3 (311-510aa)

<400> SEQUENCE: 5

```
Phe Gln Asn Val Ala Asp Leu His Leu Tyr Leu Tyr Ser Ala Lys Ala
  1               5                  10                  15

Gln Val Ser Gly Gln Ser Ala Arg Lys Met Arg Leu Gly Asp Ala Val
             20                  25                  30

Glu Gln Gly Val Ile Asn Asn Thr Val Leu Gly Tyr Phe Ile Gly Arg
         35                  40                  45

Ile Tyr Leu Tyr Leu Thr Lys Val Gly Ile Ser Pro Asp Lys Leu Arg
     50                  55                  60

Phe Arg Gln His Met Glu Asn Glu Met Ala His Tyr Ala Cys Asp Cys
 65                  70                  75                  80

Trp Asp Ala Glu Ser Lys Thr Ser Tyr Gly Trp Ile Glu Ile Val Gly
                 85                  90                  95

Cys Ala Asp Arg Ser Cys Tyr Asp Leu Ser Cys His Ala Arg Ala Thr
            100                 105                 110

Lys Val Pro Leu Val Ala Glu Lys Pro Leu Lys Glu Pro Lys Thr Val
            115                 120                 125

Asn Val Val Gln Phe Glu Pro Ser Lys Gly Ala Ile Gly Lys Ala Tyr
130                 135                 140

Lys Lys Asp Ala Lys Leu Val Met Glu Tyr Leu Ala Ile Cys Asp Glu
145                 150                 155                 160

Cys Tyr Ile Thr Glu Ile Glu Met Leu Leu Asn Glu Lys Gly Glu Phe
                165                 170                 175

Thr Ile Glu Thr Glu Gly Lys Thr Phe Gln Leu Thr Lys Asp Met Ile
                180                 185                 190

Asn Val Lys Arg Phe Gln Lys Thr
                195                 200
```

<210> SEQ ID NO 6
<211> LENGTH: 175

```
<212> TYPE: PRT
<213> ORGANISM: Homo sapiens
<220> FEATURE:
<221> NAME/KEY: DOMAIN
<222> LOCATION: (1)..(175)
<223> OTHER INFORMATION: Fragment 4 (511-685aa)

<400> SEQUENCE: 6

Leu Tyr Val Glu Glu Val Val Pro Asn Val Ile Glu Pro Ser Phe Gly
  1               5                  10                  15

Leu Gly Arg Ile Met Tyr Thr Val Phe Glu His Thr Phe His Val Arg
             20                  25                  30

Glu Gly Asp Glu Gln Arg Thr Phe Phe Ser Phe Pro Ala Val Val Ala
         35                  40                  45

Pro Phe Lys Cys Ser Val Leu Pro Leu Ser Gln Asn Gln Glu Phe Met
     50                  55                  60

Pro Phe Val Lys Glu Leu Ser Glu Ala Leu Thr Arg His Gly Val Ser
 65                  70                  75                  80

His Lys Val Asp Asp Ser Ser Gly Ser Ile Gly Arg Arg Tyr Ala Arg
                 85                  90                  95

Thr Asp Glu Ile Gly Val Ala Phe Gly Val Thr Ile Asp Phe Asp Thr
            100                 105                 110

Val Asn Lys Thr Pro His Thr Ala Thr Leu Arg Asp Arg Asp Ser Met
            115                 120                 125

Arg Gln Ile Arg Ala Glu Ile Ser Glu Leu Pro Ser Ile Val Gln Asp
        130                 135                 140

Leu Ala Asn Gly Asn Ile Thr Trp Ala Asp Val Glu Ala Arg Tyr Pro
145                 150                 155                 160

Leu Phe Glu Gly Gln Glu Thr Gly Lys Lys Glu Thr Ile Glu Glu
                165                 170                 175

<210> SEQ ID NO 7
<211> LENGTH: 528
<212> TYPE: DNA
<213> ORGANISM: Homo sapiens
<220> FEATURE:
<221> NAME/KEY: gene
<222> LOCATION: (1)..(528)
<223> OTHER INFORMATION: DNA sequence of Fragment 4

<400> SEQUENCE: 7
ctatatgtgg aagaagttgt tccgaatgta attgaacctt ccttcggcct gggtaggatc      60
atgtatacgg tatttgaaca tacattccat gtacgagaag gagatgaaca gagaacattc     120
ttcagtttcc ctgctgtagt tgctccattc aaatgttccg tcctcccact gagccaaaac     180
caggagttca tgccatttgt caaggaatta tcggaagccc tgaccaggca tggagtatct     240
cacaaagtag acgattcctc tgggtcaatc ggaaggcgct atgccaggac tgatgagatt     300
ggcgtggctt ttggtgtcac cattgacttt gacacagtga acaagacccc ccacactgca     360
actctgaggg accgtgactc aatgcggcag ataagagcag agatctctga gctgcccagc     420
atagtccaag acctagccaa tggcaacatc acatgggctg atgtggaggc caggtatcct     480
ctgtttgaag ggcaagagac tggtaaaaaa gagacaatcg aggaatga                  528
```

USES OF GRS PROTEINS OR FRAGMENTS THEREOF

CROSS-REFERENCE TO RELATED APPLICATIONS

This application is the U.S. national phase, pursuant to 35 U.S.C. §371, of PCT international application Ser. No. PCT/KR2009/005829, filed Oct. 12, 2009, designating the United States and published on Apr. 15, 2010, as publication WO/2010/041913; which claims priority to Korean Application No. 10-2008-0099784, filed Oct. 10, 2008. The entire contents of the aforementioned patent applications are incorporated herein by reference.

TECHNICAL FIELD

This application claims priority to Korean Patent Application No. 10-2008-0099784 filed on Oct. 10, 2008, which is hereby incorporated by reference herein.

The present invention relates to a novel use of glycyl-tRNA synthetase (GRS) protein, a fragment thereof, or a nucleotide encoding the same. More particularly, the present invention relates to an anticancer composition including the GRS protein, a fragment thereof, or a nucleotide encoding the same as an effective ingredient, a use of the GRS protein, a fragment thereof, or a nucleotide encoding the same for the preparation of an anticancer agent, and a method for treating cancer including administering an effective amount of the GRS protein, a fragment thereof, or a nucleotide encoding the same to a subject in need thereof.

BACKGROUND ART

Cancer refers to a disease in which a group of cells display uncontrolled growth and proliferation due to loss of the ability to differentiate. Most of cancers are explained by the multistep carcinogenesis theory describing that mutations in oncogenes and tumor suppressor genes lead to 58-steps mutations and finally generate cancer cells. It is known that activation of cancer-causing oncogenes induces abnormal proliferation of cells, and activation of tumor suppressor genes suppresses the abnormal proliferation of cells and interrupts carcinogenesis via apoptosis, kills specific cells and inhibits generation of cancer cells.

Apoptosis is a mechanism of cell death along with necrosis. In contrast to necrosis which is caused accidentally by physical trauma, toxic chemicals, etc., it can be defined as gene-directed cellular self-destruction or programmed cell death. Multicellular organisms maintain homeostasis of cell numbers through balancing of constant cell proliferation and death. Apoptosis is the process by which the cell dies under normal physiological conditions.

The process of apoptosis may be divided into three stages according to morphological and physiological changes. In the initial stage, the cell shrinks as a result of dehydration. Blebs are formed in the cell membrane, large DNAs of 50 kb or more start degradation, and intracellular calcium level increases. In the intermediate stage, DNAs are fragmented to about 180-200 bp, displaying DNA laddering on DNA electrophoresis. In the final stage, the cell membrane completely loses its functions, and the cell is engulfed by nearby cell. It is known that the number of sub-G1 hypodiploid cells is increasing as apoptosis proceeds (Nicoletti, I., Miglorati, G., Pagliacci, M. C., Grignani, F. and Riccardi, C., *J. Immunol. Methods* 139(2): 271-9, 1991; Steven W. Sherwood, James P. Sheridan and Robert T. Schimke, *Experimental Cell Research* 215: 373-379, 1994).

Apoptosis is involved in normal development and differentiation of organisms, such as the degeneration of the tadpole tail, and is frequently seen during differentiation of fingers and toes in an embryo, menstruation, and formation of synapses between neural cells in the brain. Also, it is related with the maintenance of homeostasis, and is involved in the removal of cells infected by viruses by cytotoxic T lymphocytes.

Recently, it was found out that the suppression of cancer cell proliferation is related to the induction of apoptosis. Currently employed radiotherapies and chemotherapies, e.g. 5FU, Adriamycin and taxol, induce apoptosis in human cancer cells in vitro (K. Sugamura et al., *Cancer* 79: 12, 1997; S. M. Tu et al., *Cancer Lett.* 93: 147, 1995; R. M. Gangemi et al., *Science* 784: 550, 1990).

Thus, researches on substances that can induce apoptosis in cancer cells for use as anticancer agent are actively carried out. For example, Korean Patent Publication No. 2004-59495 discloses a composition inducing apoptosis of cancer cells, which includes *Agaricus* extract, and Korean Patent Publication No. 2001-7007571 discloses 7-aryl-6(Z)-heptatrienoic acid retinamide as a compound inducing apoptosis of cancer cells. However, these anticancer agents are not widely used. In addition, they are known to kill not only the cancer cells but also normal cells.

Although the glycyl-tRNA synthetase (GRS) protein is known as a protein involved in the synthesis of aminoacyl tRNA, nothing is known about the anticancer activity of the protein.

DISCLOSURE

Technical Problem

While the inventors of the present invention have carried out researches on proteins having anticancer activity, they confirmed that GRS proteins or fragments thereof have activity to induce apoptosis of cancer cell specifically thereby completing the present invention.

Accordingly, the object of the present invention is to provide an anticancer composition comprising a GRS protein or fragment thereof as an active ingredient.

Also, another object of the present invention is to provide an anticancer composition comprising a nucleic acid encoding a GRS protein or fragment thereof as an active ingredient.

Also, still another object of the present invention is to provide use of a GRS protein or fragment thereof for preparing an agent for anticancer drug.

Also, still another object of the present invention is to provide use of a nucleic acid encoding a GRS protein or fragment thereof for preparing an agent for anticancer drug.

Also, still another object of the present invention is to provide a method for treating cancer administering to a subject in need thereof an effective amount of a GRS protein or fragment thereof.

Also, still another object of the present invention is to provide a method for treating cancer administering to a subject in need thereof an effective amount of a nucleic acid encoding a GRS protein or fragment thereof.

Technical Solution

To achieve the above object, the present invention provides an anticancer composition comprising a GRS (glycyl-tRNA-synthetase) protein or fragment thereof as an active ingredient.

Also, the present invention provides an anticancer composition comprising a nucleic acid encoding a GRS (glycyl-tRNA-synthetase) protein or fragment thereof as an active ingredient.

Also, the present invention provides use of a GRS (glycyl-tRNA-synthetase) protein or fragment thereof for preparing an agent for anticancer drug.

Also, the present invention provides use of a nucleic acid encoding a GRS (glycyl-tRNA-synthetase) protein or fragment thereof for preparing an agent for anticancer drug.

Also, the present invention provides a method for treating cancer administering to a subject in need thereof an effective amount of a GRS (glycyl-tRNA-synthetase) protein or fragment thereof.

Also, the present invention provides a method for treating cancer administering to a subject in need thereof an effective amount of a nucleic acid encoding a GRS (glycyl-tRNA-synthetase) protein or fragment thereof.

Hereafter, the present invention is described in detail.

The anticancer composition of the present invention comprises glycyl-tRNA synthetase (GRS) protein or a fragment thereof as an effective ingredient.

Since the GRS protein or a fragment thereof has the activity of specifically inducing apoptosis of cancer cells, it can be effectively used as the effective ingredient of the anticancer composition.

In order to investigate whether the GRS protein has the activity of specifically inducing apoptosis of cancer cells, the inventors of the present invention confirmed that the GRS protein is specifically secreted from macrophages in serum-starved condition (Example 1).

Also, the inventors confirmed that, when macrophages and cancer cells are treated with Adriamycin which induces apoptosis by intercalating DNA, only the macrophages specifically secrete the GRS protein (Example 2-1). Further, it was confirmed that the GRS protein is specifically secreted only from the macrophages in glucose-starved condition under which apoptosis can be induced (Example 2-2).

Based on the finding that the GRS protein is secreted only from the macrophages during apoptosis, the inventors investigated whether the GRS protein has anticancer activity. First, it was confirmed that the GRS protein secreted from the macrophages is attached to the surface of another cell (Example 3). Further, through FACS or MTT assay, it was confirmed that the GRS protein specifically kills the cancer cells without harming normal neural cells, immune cells, or kidney cells (Examples 4-1 and 4-2). And only if cancer cells were treated with the GRS protein, caspase 3 in active form was observed, suggesting that apoptosis is induced by DNA fragmentation (Example 4-3). In addition, the inventors investigated the specific mechanism by which the GRS protein induces the apoptosis of the cancer cells. It was found out that the GRS protein induces the apoptosis of the cancer cells by affecting the p38 kinase which is known to be involved in cell growth or apoptosis.

Further, in order to investigate the effect of GRS on signaling molecules, the inventors treated HeLa cells with GRS and examined its effect on mitogen-activated protein kinases (MAPKs) such as extracellular-signal regulated kinase (ERK), p38 MAPK and Jun N-terminal kinase. It was revealed that phosphorylated ERK and p38 MAPK decrease with time upon treatment with the GRS protein. In contrast, TNF-α phosphorylated all the three MAPKs, suggesting that GRS operates via a different mechanism from that of TNF-α in HeLa cells. Further, the inventors investigated whether the apoptosis induced by the GRS protein is related with mitochondria. It was revealed that GRS results in decreased level of the anti-apoptotic mediator Bax and Bcl-2 and promotes secretion of cytochrome C, confirming the pro-apoptotic activity of GRS in HeLa cells (Example 6).

Finally, in order to investigate the portion of the GRS protein having cytokine activity, the inventors prepared four fragments of the GRS protein as shown in FIGS. 13 and 14, and cell viability was examined after treating HeLa and RAW 264.7 cells with three of the fragments except for the insoluble fragment. As a result, it was confirmed that the fragment 4 of SEQ ID NO. 6 has pro-apoptotic cytokine activity. The fragment 4 consists of 511st through 685th amino acids of the full-length GRS. It includes the C-terminal anticodon-binding domain (511st through 674th amino acids).

Accordingly, since the GRS protein or a fragment thereof has the activity of specifically inducing apoptosis of cancer cells, it can be effectively used as an effective ingredient of an anticancer composition.

The GRS protein or a fragment thereof included in the anticancer composition of the present invention refers to a wild-type or recombinant GRS protein, or a protein having a substantially equivalent physiological activity. The protein having the substantially equivalent physiological activity includes a functional equivalent and a functional derivative of the wild-type/recombinant GRS protein or a fragment thereof.

The "functional equivalent" refers to an amino acid sequence variant with all or part of the amino acids of the wild-type protein substituted, deleted or added and having a substantially equivalent physiological activity as that of the wild-type GRS protein or a fragment thereof. The "functional derivative" refers to a protein or a fragment thereof modified to improve or reduce physical/chemical properties of the GRS protein or a fragment thereof and having a substantially equivalent physiological activity as that of the wild-type GRS protein.

The GRS protein or a fragment thereof may be derived from a mammal. Specifically, the mammal may include human. Most specifically, the GRS protein or a fragment thereof may be a polypeptide having an amino acid sequence of SEQ ID NO. 1 or SEQ ID NOs. 3 to 6. SEQ ID NO. 1 is the acid sequence of the GRS protein, and SEQ ID NOs. 3 to 6 are those of the fragments of the GRS protein.

The GRS protein or a fragment thereof may be prepared through a genetic engineering technique (Park et al., *J. Biol. Chem.* 274: 166673-166676, 1999).

Meanwhile, an anticancer composition of the present invention comprises a nucleic acid encoding a GRS protein or a nucleic acid (or a polynucleotide), and comprises a expression vector including a promoter and a polynucleotide encoding a GRS protein or fragment thereof operably linked to the promoter.

The term "expression vector" as used herein refers to a vector capable of expressing a target protein or target RNA in an adequate host cell, and refers to a genetic construct containing essential regulatory elements to which a gene insert is operably linked in such a manner as to be expressed. Proper expression vectors comprise a signal sequence for membrane targeting or secretion or leader sequence as well as a promoter, an operator, an initiation codon, a termination codon, a polyadenylation signal and an enhancer (enhancing gene) and may be prepared variously according to the purpose. Also, an expression vector comprise a selective marker for selecting host cells which include the vector and in case of a replicable vector, it comprise replication origins. An expression vector of the present invention comprises polynucleotide encoding a GRS protein of the present invention or a fragment thereof and it is operably linked to the promoter. The "promoter" of the present invention means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment.

A nucleic acid encoding the GRS protein or the fragment thereof comprises DNA or RNA. Preferably, it refers DNA originated from mammals, more preferably it refers DNA encoding a GRS protein or the fragment thereof originated from human beings. Most preferably, the nucleic acid encoding a GRS protein or the fragment thereof may have nucleotide sequence of SEQ ID NOs. 2 or 7.

The nucleic acid may be introduced as a phenotype to target cell by infection or transduction or a technique which is well known in the art after introducing it to plasmid or viral vector with a technique which is well known in the art.

The plasmid expression vector is a method for introducing a gene to human which is proved from FDA and it introduces plasmid DNA directly to human cell (Nale, E. G., et. al., Science, 249:1285-1288, 1990). The plasmid DNA has advantage of even purification compared with viral vectors. As useful plasmid expression vectors for the present invention, there are mammalian expression plasmid which are well known in the art. For example, but not limited thereto, pRK5 (European Patent No. 307,247), pSV16B (PCT Publication No. 91/08291) and pVL1392 (PharMingen) are representative.

A plasmid expression vector comprising a nucleic acid of the present invention may be introduced to cancer cells by techniques well known in the art such as transient transfection, microinjection, transduction, cell fusion, calcium phosphate precipitation, liposome-mediated transfection, electroporation, gene gun and other techniques for influxing DNA to a cell (Wu et al., J. Bio. Chem., 267:963-967, 1992; Wu and Wu, J. Bio. Chem., 263:14621-14624, 1998).

As viral expression vectors, but not limited thereto, there are retroviral expression vectors, adenoviral expression vectors, herpes viral expression vectors and avipox viral expression vectors. The retroviral expression vectors are constructed by eliminating or modifying all of viral genes and therefore non-viral protein can be prepared from the cells by infection of viral vectors. Main advantages of the retroviral vector for gene therapy are to introduce large quantity of a gene to a cloning cell and integrate the gene exactly to cellular DNA, and not to occur continuous infection after gene infection (Miller, A. D., Nature, 1992, 357:455-460). FDA proved retroviral vector is prepared by PA317 amphotrophic retroviral package cell (Miller, A. D. and Buttimore, C., Molec. Cell Biol., 6:2895-2902, 1986). As non-retroviral vectors, there is adenovirus as mentioned above (Rosenfeld, M. A., et al., Cell, 68:143-155, 1992; Jaffe, H. A. et al., Nature Genetics, 1:372-378, 1992; Lemarchand, P. et al., Proc. Natl. Acad. Sci. USA, 89:6482-6486, 1992) Main advantages of the adenovirus are to transfer large molecular DNA fragment (36 Kb genome) and to infect non-cloning cell with very high titer. Also, herpes virus may be useful for human gene therapy (Wolfe, J. H., et al., Nature Genetics, 1:379-384, 1992). In addition, proper viral vectors which are well known in the art can be used for an anticancer composition of the present invention.

The vector expressing a GRS protein or a fragment thereof may be administered by a method well known in the art. For example, it may be administered partially, parenterally, orally, nasally, intravenously, intramuscularly, subcutaneously or by proper method. Particularly, the expression vector may be injected directly into a target cancer cell at an effective amount for treating the target tissue. Particularly for a cancer presented in a body cavity such as in the eye, gastrointestinal tract, genitourinary tract, pulmonary and bronchial system and so on, the inventive pharmaceutical composition can be injected directly into the hollow organ which affected by the cancer using a needle, a catheter or other delivery tubes. Any effective imaging device, such as X-ray, sonogram, or fiberoptic visualization system, may be used to locate the target tissue and guide the needle or catheter tube. In addition, the pharmaceutical composition of the present invention may be administered into the blood circulation system for a cancer which cannot be directly reached or anatomically isolated.

An anticancer composition of the present invention refers, but not limited thereto, a pharmaceutical composition. The pharmaceutical composition of the present invention may be formulated to a proper formulation with a pharmaceutically acceptable carrier. The term "pharmaceutically acceptable" means what is physiologically acceptable and, when administered to human beings, generally does not cause allergic reactions, such as gastrointestinal disorder and dizziness, or similar reactions thereto. A pharmaceutically acceptable carrier, for example, carriers for oral preparation comprise lactose, starch, cellulose derivatives, magnesium stearate, stearic acid, and carriers for parenteral preparation comprise water, oil, saline, aqueous glucose and glycol, and stabilizers and preservatives may further be comprised. The example of the stabilizers may be an antioxidant such as sodium hydrogen sulfite, sodium sulfite, and ascorbic acid. The example of the preservatives may be benzalkonium chloride, methyl- or prophyl-paraben, and chlorobutanol. The list of pharmaceutically acceptable carriers is disclosed in Remington's Pharmaceutical Sciences, 19th ed., Mack Publishing Company, Easton, Pa., 1995.

The present invention provides use of a GRS protein or a fragment thereof for preparing an anticancer agent.

Also, the present invention provides use of a nucleic acid encoding a GRS protein or a fragment thereof for preparing an anticancer agent.

A pharmaceutical composition of the present invention may be formulated into, but not limited thereto, intaking tablet, troche, capsule, elixir, suspension, syrup, wafer and the like for an oral administration formulation by mixing a nucleic acid of the present invention and a pharmaceutically acceptable salt with an excipient. These preparations may also comprise diluents (e.g., lactose, dextrose, sucrose, mannitol, sorbitol, cellulose and/or glycine), lubricants (e.g., silica, talc, stearic acid and a magnesium or calcium salt thereof, and/or polyethylene glycol) in addition to the active ingredient. Among various preparations, tablets may also comprise binders, such as magnesium aluminum silicate, starch pastes, gelatin, tragacanth, methylcellulose, sodium carboxymethylcellulose and/or polyvinylpyrrolidone, and, if desired, may further comprise disintegrating agents, such as starches, agar or alginic acid or a sodium salt thereof, heterogenous mixtures and/or absorbents, colorants, flavors and sweeteners. The said composition may be prepared by mixing, granulization or coating. An injectable preparation may be prepared according to techniques well known in the art by using a proper dispersing reagent or a humectant and suspension reagent. For example, each ingredient may be formulated to an injectable preparation by dissolving it to saline or buffer solution. Also, in case of parenteral administration, it may be prepared in the forms of injectable preparations, creams, lotions, ointments, oils, humectant, gels, aerosol, and nasal inhalations by the method well known in the art. The formulation of the above-mentioned is well described in Remington's Pharmaceutical Science, 15th Edition, 1975, Mack Publishing Company, Easton, Pa. 18042, Chapter 87: Blaug, Seymour.

The present invention provides a method for treating cancer administering an effective amount of a GRS protein or fragment thereof to a subject in need.

The present invention provides a method for treating cancer administering an effective amount of a nucleic acid encoding a GRS protein or fragment thereof to a subject in need.

A pharmaceutical composition prepared by the method above may be administered through various routes as well as orally, subcutaneous, intravenous and intramuscular. As used herein, the term "effective amount" refers to the amount showing effect on treating of cancer and as used herein, the term "subject" means animals, preferably, it means mammals, particularly animals including human beings and it may be a cell, tissue and organ originated from an animal. The subject may be patients in need of treatment.

A pharmaceutical composition of the present invention may be administered as itself alone or as various forms of preparations as mentioned above. Preferably, it may be administered until it shows desired effect, that is, apoptosis of endothelial cells and/or anticancer activity. A pharmaceutical composition of the present invention may be administered various routes according to the skills well known in the art. That is, it may be administered orally or parenterally, for example, by bucaly, intramuscularly, intravenously, intracutaneously, intraarterialy, intramarrowly, subduraly, intraperitonealy, intranasally, intravaginally, intrarectumly, sublingually or rectumly, or into gastrointestinal tracts, mucosal layers or respiratory organs. For example, an injectable form of the polypeptide of the present invention may be administered by lightly pricking the skin with 30-gauge injection needle, or applying directly into the skin. Preferably, a pharmaceutical composition of the present invention may be administered directly to skin. Also, a pharmaceutical composition of the present invention may be administered by binding to a molecule inducing highly affinitive binding to target cells or tissue (e.g.: skin cell or skin tissue) or by formulated into a capsule in the molecule. A pharmaceutical composition of the present invention may bind with sterols (e.g. cholesterol), lipids (e.g. cataion lipid, virosome, and liposome) or binding complexes specific to target cell (e.g. ligand which are recognized by specific receptors of target cells). Proper coupling reagents or cross-linking reagents may comprise, for example, protein A, carbodimide, Succinimidyl 3-(2-pyridyldithio)propionate (SPDP) and the like. Total effective amount of the polypeptide of the present invention may be administered to a patient with a single dose, or may be administered with multiple doses by fractionated treatment protocol. The pharmaceutical compositions of the present invention may contain variable amount of effective ingredient according to the administration purpose. However, normally, it may be administered many times a day with amount of 0.1 ug to 1 g/kg body weight/day.

However, the dose may be suitably determined by considering various factors, such as age, body weight, health condition, sex, disease severity, diet and excretion of a subject in need of treatment, as well as administration time and administration route. Therefore, when those are considered, skilled person in the art may determine appropriate dose for a certain use. A pharmaceutical composition of the present invention may not limit formulations, administration routes, and administration methods as long as they show the effect of the present invention.

The anticancer composition of the present invention is very effective in treatment of cancer. The cancers comprise, but not limited thereto, breast cancer, colorectal cancer, lung cancer, small cell lung cancer, stomach cancer, liver cancer, leukemia, bone cancer, pancreatic cancer, skin cancer, head or neck cancer, malignant melanoma of skin or ocular, uterine cancer, ovarian cancer, rectal cancer, cancer around anal, colon cancer, breast cancer, fallopian tubular cancer, endometrial carcinoma, cervical cancer, vaginal cancer, vulval cancer, Hodgkin's disease, esophagus cancer, small intestinal cancer, endocrine glandular cancer, thyroid cancer, parathyroid cancer, adrenal cancer, soft tissue sarcoma, urethra cancer, testis cancer, prostate cancer, acute or chronic leukemia, lymphocyte lymphoma, bladder cancer, kidney or ureter cancer, kidney cell cancer, kidney pelvis cancer, CNS tumor, primary CNS lymphoma, spinal cord tumor, brain-stem gliomas, pituitary adenoma or combination thereof.

Advantageous Effects

As can be seen foregoing, since the GRS proteins or fragments thereof have activity to induce apoptosis of cancer cell specifically, a composition comprising the GRS proteins or fragments thereof or a nucleic acid encoding thereof may be useful to treat cancer.

MODE FOR INVENTION

Figure 1:
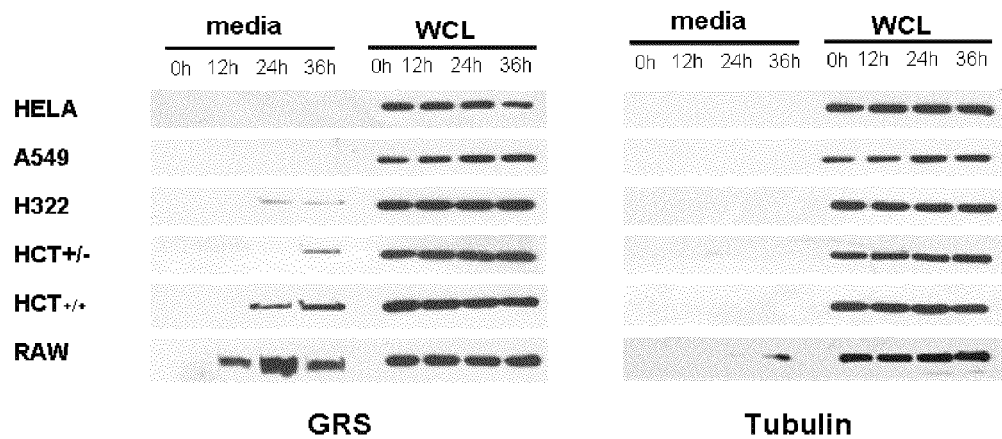
FIG. 1 shows a result of investigating whether glycyl-tRNA synthetase (GRS) protein is secreted specifically from macrophages in serum-starved condition through Western blotting (WCL: whole cell lysate)

The examples and experiments will now be described. The following examples and experiments are for illustrative purposes only and not intended to limit the scope of the present invention.

Example 1

Confirmation of Secretion of GRS Protein from Macrophages in Serum-Starved Condition HeLa, A549, H322, HCT+/− and HCT+/+ cancer cells and macrophage RAW cells were placed on a 35-mm dish, cultured for 18 hours, and then washed with serum-starved medium (1 mL). 0, 12, 24 and 36 hours after the washing, proteins were collected from the medium and the whole cell lysate, and it was investigated whether the GRS protein was secreted from the cells through Western blotting using anti-GRS anti-tubulin antibodies.

Specifically, in order to collect the proteins from the medium, the cell culture was centrifuged at a rate of 3000 rpm at 4° C. for 10 minutes. Then, after centrifuging further at a rate of 20,000 g at 4° C. for 15 minutes and separating the supernatant, 100% trichloroacetic acid (TCA, 100 µL) was added thereto (final concentration=10%). After incubating overnight at 4° C. to precipitate the protein, centrifugation was carried out at a rate of 18,000 g at 4° C. for 10 minutes. After decanting the supernatant, adding 100 mM HEPES (pH 8.0, 55 µL) and vortexing for 5 seconds, 5× sample buffer (15 µL) was added to collect the protein from the medium.

Meanwhile, in order to collect proteins from the whole cell lysate, a solution (200 µL) containing 0.5% Triton X-100, 2 mM EDTA, 10% glycerol, 150 mM NaCl, 25 mM Tris-HCl (pH 7.4) and protease inhibitor was added to the dish containing the cells. After incubation at 4° C. for 30 minutes and centrifugation at a rate of 12,000 rpm at 4° C. for 15 minutes, the protein was quantified by the Bradford method.

The collected protein was separated by loading on 8% SDS-PAGE and Western blotting was carried out using anti-GRS and anti-tubulin antibodies. The result is shown in FIG. 1.

As seen from FIG. 1, the GRS protein (SEQ ID NO. 1) was secreted from the macrophages in serum-starved condition, but it was hardly secreted from the cancer cells. In contrast to tubulin, the GRS protein was secreted specifically from the macrophage. Especially, the GRS protein was secreted from the macrophage after the serum-starved condition was maintained for 12 hours.

Example 2

Secretion of GRS Protein from Macrophages During Induced Apoptosis

<2-1> After Treatment with Adriamycin

Given the result that the GRS protein is secreted only after the serum-starved condition is prolonged, it was investigated whether the secretion of the GRS protein is because of apoptosis or loss of the aminoacyl activity of the GRS protein. Specifically, HeLa and HCT+/− cancer cells and macrophage RAW cells were placed on a 35-mm dish, cultured for 18 hours, washed with serum-starved medium (1 mL), and then treated with 1 µg/mL Adriamycin. 0, 0.5, 1, 2 and 4 hours after the treatment, proteins were collected from the medium and the whole cell lysate, and it was investigated whether the GRS protein was secreted from the cells through Western blotting using anti-GRS anti-tubulin antibodies, in the same manner as in Example 1. The result is shown in FIG. 2A.

Figure 2:
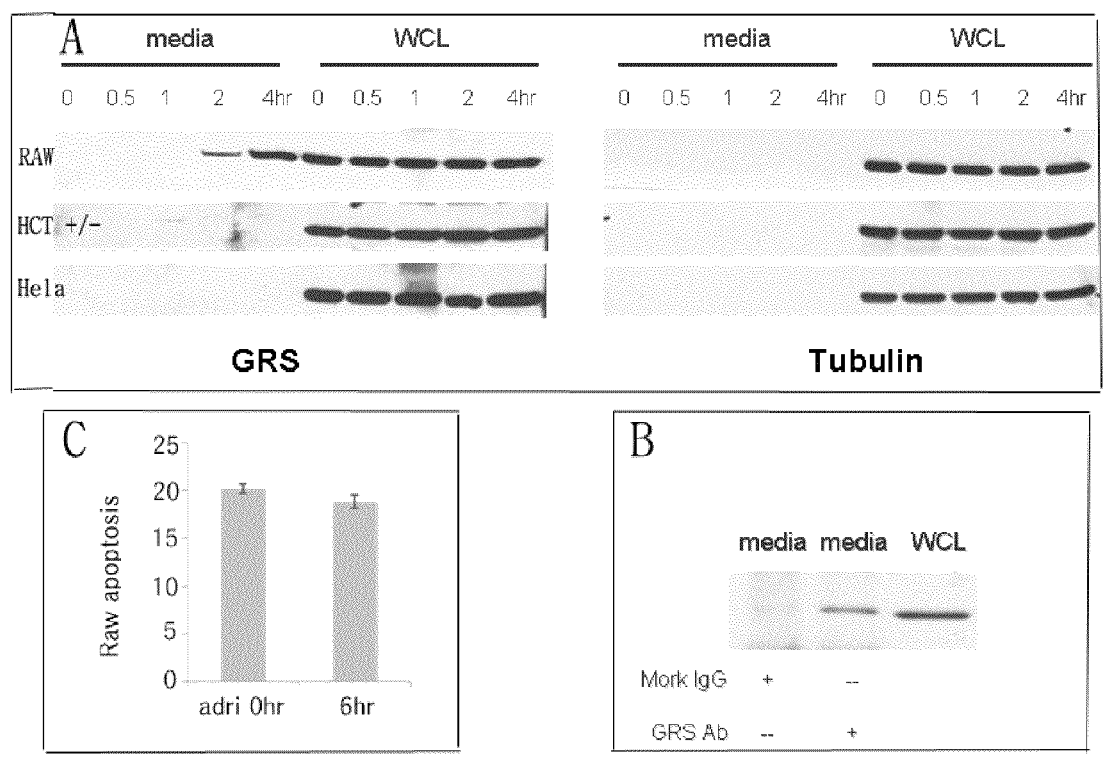
FIG. 2 shows a result of investigating whether the GRS protein is secreted from the macrophages during apoptosis induced by Adriamycin (WCL: whole cell lysate)

As seen from FIG. 2A, the GRS protein was specifically secreted only from the macrophages as in Example 1 when apoptosis was induced by Adriamycin.

Immunoprecipitation assay was performed to confirm whether the secreted protein is the GRS protein. 4 hours after the treatment with Adriamycin, anti-GRS antibody (1.5 µg) was added to collect the protein from the medium. After incubation at 4° C. for 2 hours and washing with PBS, protein agarose A (25 µL) was added. Then, after incubation at 4° C. for 4 hours and centrifugation at a rate of 2,800 rpm at 4° C. for 2 minutes, the supernatant was decanted and the remainder was washed with PBS (1 mL). After repeating this procedure 3 times, sample buffer (65 µL) was added and mixed for 5 seconds and Western blotting was performed in the same manner as in Example 1. Further, proteins were collected from the whole cell lysate in the same manner as in Example 1. The Western blotting result is shown in FIG. 2B.

As seen from FIG. 2B, the secreted protein was identified as the GRS protein.

Given the above results, it was further investigated whether the secretion of the GRS protein from the macrophages is simply because the cells were completely dead or it is secreted to perform a specific functionality. Specifically, 0 or 6 hours after the treatment with Adriamycin, the medium was treated with trypsin EDTA to extract cells, which were centrifuged at a rate of 500 g for 10 minutes. After decanting the supernatant and resuspending the cells in cold PBS (0.3 mL), cold 100% EtOH (0.7 mL) was added and mixed for 5 seconds, and the cells were incubated at −20° C. overnight. The cell culture was centrifuged at a rate of 500 g for 10 minutes. After decanting the supernatant, adding cold PBS (1 mL) and mixing for 5 seconds, the mixture was centrifuged again at a rate of 500 g at 4° C. for 10 minutes. Then, after decanting the supernatant and resuspending the cells in P.I solution (500 µL), they were incubated at room temperature for 20 minutes. Then, the number of dead cells was counted by FACS. The result is shown in FIG. 2C (The cells in sub-G1 phases were considered as dead cells).

As seen from FIG. 2C, the secretion of the GRS protein from the macrophages during the apoptosis induced by Adriamycin is not simply because the cells were completely dead but it is secreted to perform a specific functionality.

<2-2> In Glucose-Starved Condition

Since cancer cells can develop a glucose-starved condition around them and induce apoptosis of immune cells flocking to kill the cancer cells, it was investigated whether the GRS protein is secreted in glucose-starved condition. For this, experiment was performed in glucose-starved condition in the same manner as Example 1. The result is shown in FIG. 3A.

Figure 3:
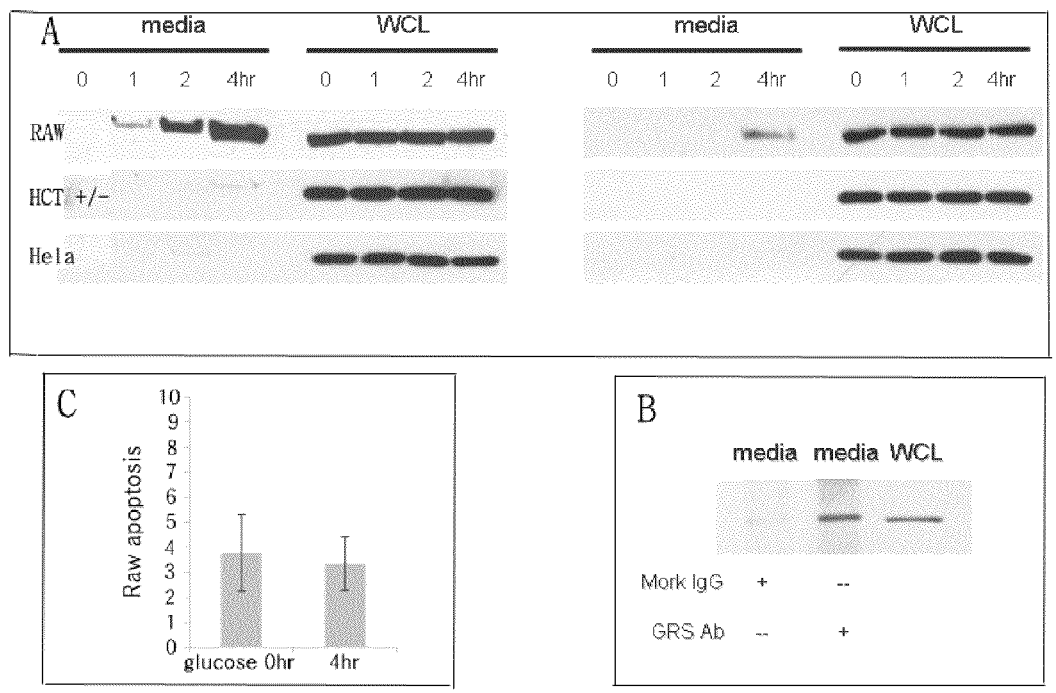
FIG. 3 shows a result of investigating whether the GRS protein is secreted from the macrophages during apoptosis induced by glucose deficiency (WCL: whole cell lysate)

As seen from FIG. 3A, the GRS protein was specifically secreted only from the macrophages as in Example 1.

Further, experiment was performed in the same manner as Example 2 in order to investigate whether the secreted protein was the GRS protein. The result is shown in FIG. 3B.

As seen from FIG. 3B, the secreted protein was identified as the GRS protein.

Given the above results, it was investigated in the same manner as in Example 2 whether the secretion of the GRS protein from the macrophages is simply because the cells were completely dead or it is secreted to perform a specific functionality. The result is shown in FIG. 3C.

As seen from FIG. 3C, the secretion of the GRS protein from the macrophages during the apoptosis induced by glucose deficiency is not simply because the cells were completely dead but it is secreted to perform a specific functionality.

Example 3

Confirmation of Attachment of GRS Protein to Cells

HeLa and HCT+/− cancer cells, normal 293 cells and macrophage RAW cells were placed on a 35-mm dish, cultured for 18 hours, and then washed with serum-starved medium (1 mL). Then, after adding 0, 1, 2, 5 or 10 μg of biotinylated GRS protein, proteins were collected from the whole cell lysate in the same manner as in Example 1. Then, Western blotting was performed using streptavidin-HRP and anti-tubulin antibodies. The result is shown in FIG. 4.

Figure 4:
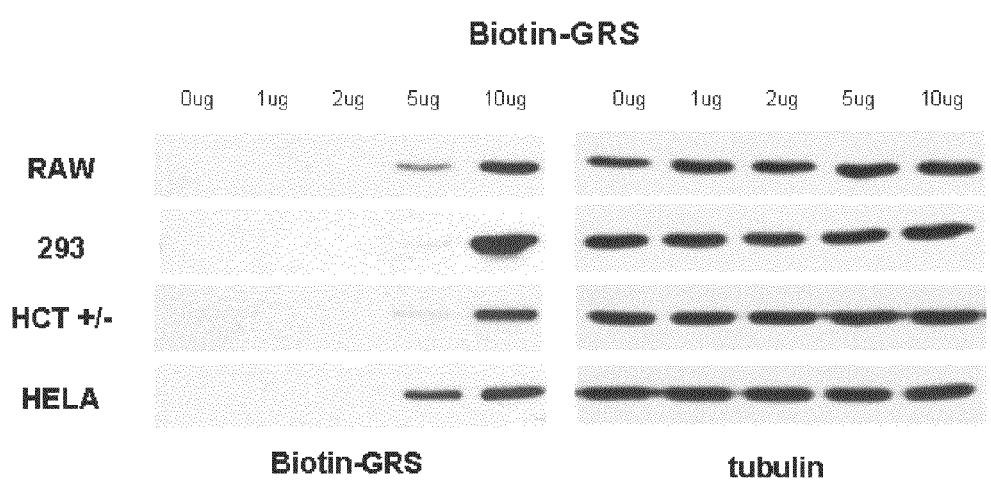
FIG. 4 shows a result of investigating whether the GRS protein secreted from the macrophages is attached to cancer cells.

As seen from FIG. 4, the GRS protein secreted from the macrophages was attached to the surface of other cells. Thus, further experiment was carried out in order to investigate what functionality can be performed by the GRS protein.

Example 4

Anticancer Activity of GRS Protein

<4-1> Measurement of Anticancer Activity of GRS Protein by FACS

HeLa, A549, HCT+/− and HCT+/+ cancer cells, BV2 and SH-SY5Y neural cells, human skin fibroblast HSF cells, and macrophage RAW cells were placed on a 35-mm dish, and cultured for 18 hours. The cell culture was washed with serum-starved medium (1 mL), treated with GRS protein (0 or 100 nM), heated GRS protein (100 nM) or 1 μg/mL Adriamycin, and further treated with trypsin EDTA. The cells were isolated and centrifuged at a rate of 500 g for 10 minutes. After decanting the supernatant, the cells were resuspended in cold PBS (0.3 mL). After adding cold 100% EtOH (0.7 mL) and mixing for 5 seconds, the mixture was incubated at −20° C. overnight. The cell culture was centrifuged at a rate of 500 g at 4° C. for 10 minutes. After decanting the supernatant, adding cold PBS (1 mL) and mixing for 5 seconds, the mixture was centrifuged again at a rate of 500 g at 4° C. for 10 minutes. After decanting the supernatant, the cells were resuspended in P.I solution (500 μL) and incubated at room temperature for 20 minutes. Then, the number of dead cells was counted by FACS by measuring the quantity of DNA fragments resulting from apoptosis. The result is shown in FIG. 5 (The cells in sub-G1 phases were considered as dead cells).

Figure 5:
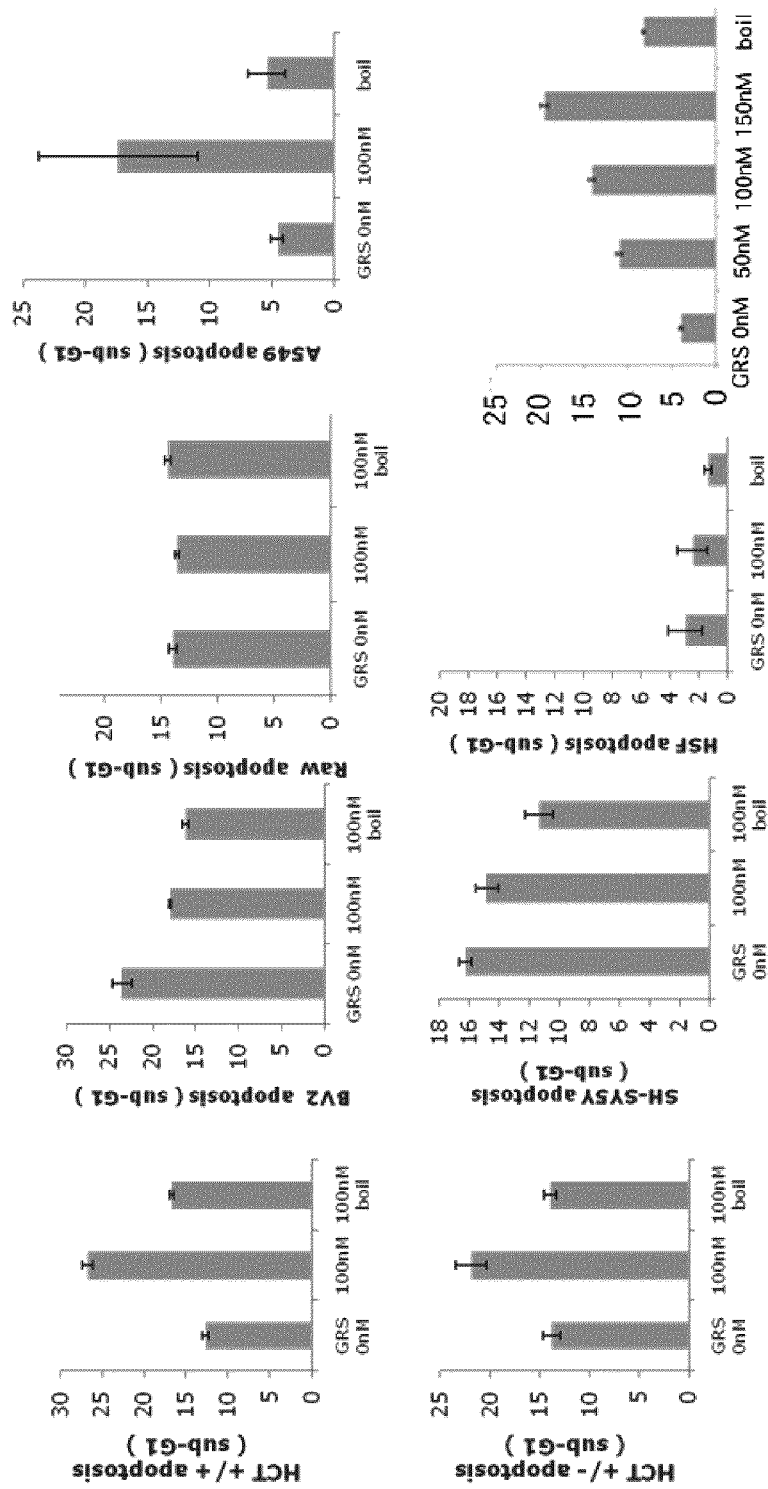
FIG. 5 shows FACS results showing that the GRS protein has specific anticancer activity.

As seen from FIG. 5, the GRS protein specifically killed only the HeLa, A549, HCT+/− and HCT+/+ cancer cells, with little effect on the neural and immune cells. Accordingly, since the GRS protein induces apoptosis of the cancer cells only, it can be used as an effective ingredient of an anticancer composition.

<4-2> Measurement of Anticancer Activity of GRS Protein by MTT Assay

HeLa, A549, HCT+/− and H460 cancer cells, H293 kidney cells, SH-SY5Y neural cells, human skin fibroblast HSF cells, and macrophage RAW cells were placed on a 96-well plate, cultured for 18 hours, washed with serum-starved medium, treated with His-GRS protein (0, 50, 100 or 150 nM), heated His-GRS protein (150 nM) or 2 μg/mL Adriamycin in serum-starved medium (100 μL), cultured for 24 hours, treated with 5 mg/mL MTT (10 μL per each well), and then cultured for 2 hours. After decanting the supernatant using a syringe and treating with DMSO (100 μL per each well), the cells were cultured for 10 minutes and absorbance was measured at 570 nM using an ELISA reader. The result is shown in FIG. 6.

Figure 6:
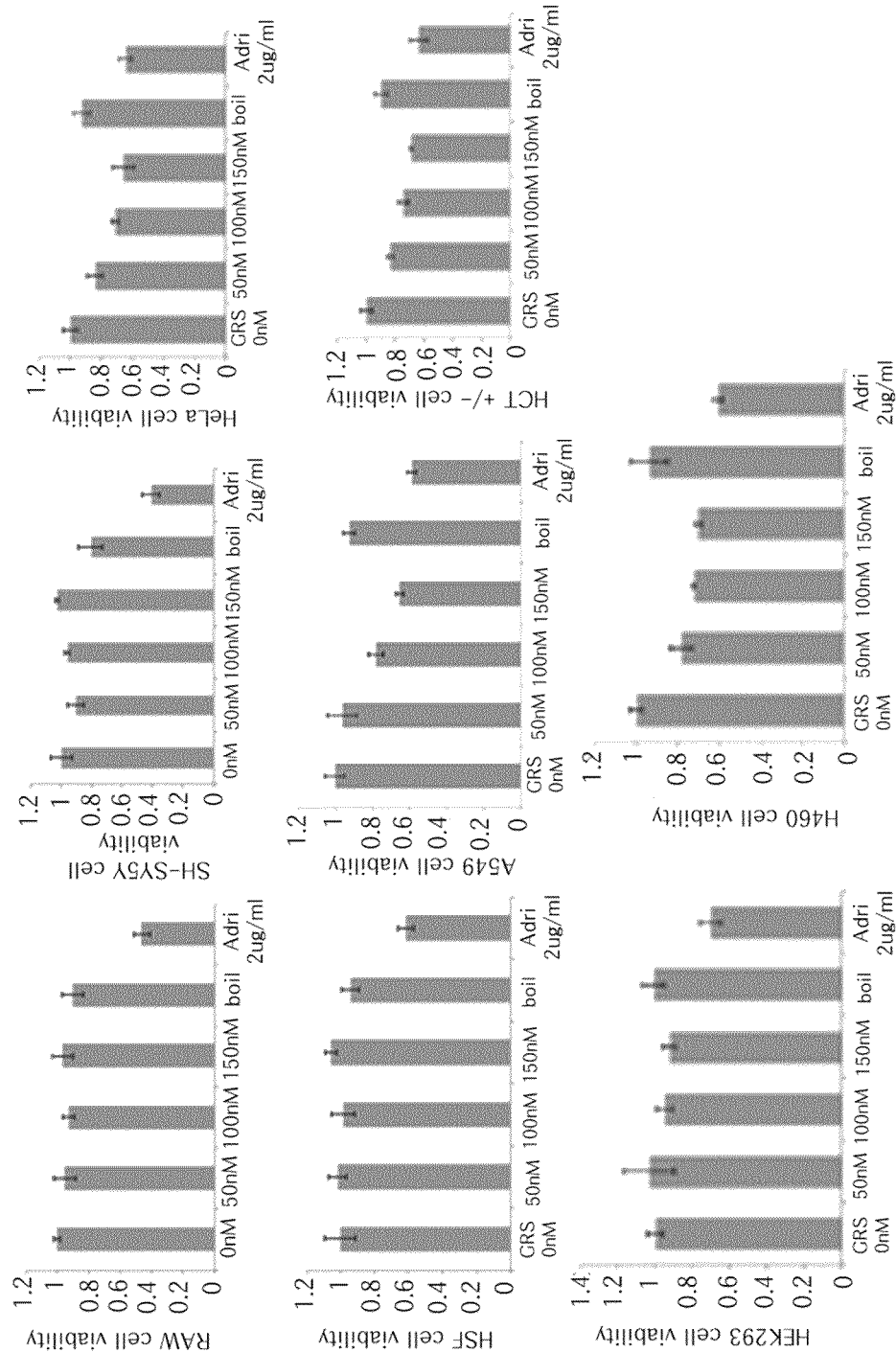
FIG. 6 shows MTT assay results showing that the GRS protein has specific anticancer activity.

As seen from FIG. 6, as a result of confirming the catalytic activity of the mitochondria through the cell viability by MTT assay, the GRS protein specifically killed the HeLa, A549, HCT+/− and H460 cancer cells, with little effect on the kidney, neural and immune cells. Accordingly, since the GRS protein induces apoptosis of the cancer cells only, it can be used as an effective ingredient of an anticancer composition.

<4-3> Measurement of Anticancer Activity of GRS Protein by Caspase 3 Assay

HCT+/− cancer cells or macrophage RAW cells were placed on a 35-mm dish. 18 hours later, after washing with serum-starved medium, the cells were treated with His-GRS protein (0, 50 nM, 100 nM or 150 nM) or heated His-GRS protein (150 nM) in serum-starved medium (1 mL). After culturing for 24 hours, the cells were collected using a lifter. The cells were centrifuged at 3000 rpm for 5 minutes and, after decanting the supernatant, adding lysis buffer (200 μL) containing 0.5% Triton X-100, 2 mM EDTA, 10% glycerol, 150 mM NaCl, 25 mM Tris-HCl (pH 7.4) and protease inhibitor, and mixing at 4° C. for 30 minutes, the mixture was centrifuged at a rate of 12,000 rpm at 4° C. for 15 minutes and the protein was quantitated by the Bradford method. The collected protein was separated by loading on 15% SDS-PAGE and Western blotting was carried out using anti-caspase 3 and anti-tubulin antibodies. The result is shown in FIG. 7.

Figure 7:
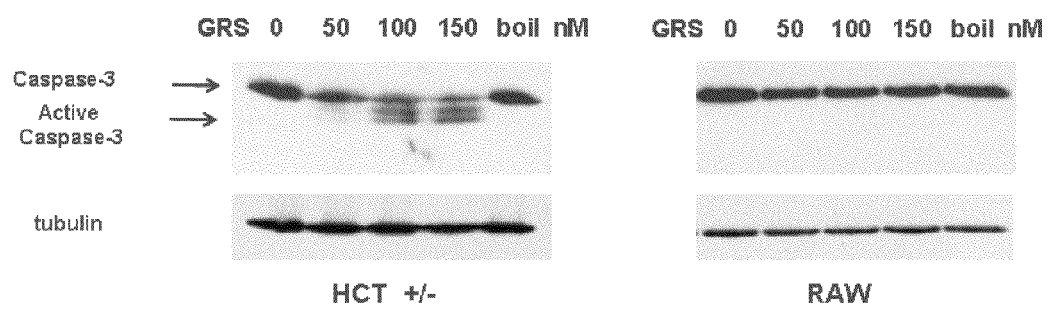
FIG. 7 shows a result of caspase 3 assay showing that the GRS protein has specific anticancer activity.

As seen from FIG. 7, caspase 3 in active form was observed when the cancer cells were treated with the GRS protein. This suggests that apoptosis is induced by DNA fragmentation. Accordingly, since the GRS protein induces apoptosis of the cancer cells only, it can be used as an effective ingredient of an anticancer composition.

Example 5

Apoptosis Mechanism of Cancer Cells by GRS Protein

HCT+/− cancer cells were placed on a 5-mm dish. 18 hours later, after washing with serum-starved medium, the cells were treated with 100 nM GRS protein or 2 μg/mL lipopolysaccharide (LPS) in serum-starved medium (1 mL). After culturing for 0, 10, 30, 60, 90 or 120 minutes, the cells were collected using a lifter. The cells were centrifuged at 3,000 rpm for 5 minutes and, after decanting the supernatant, adding lysis buffer (200 μL) containing 0.5% Triton X-100, 2 mM EDTA, 10% glycerol, 150 mM NaCl, 25 mM Tris-HCl (pH 7.4) and protease inhibitor, and mixing at 4° C. for 30 minutes, the mixture was centrifuged at a rate of 12,000 rpm at 4° C. for 15 minutes and the protein was quantitated by the Bradford method. The collected protein was separated by loading on 10% SDS-PAGE and Western blotting was carried out using anti-p-p38, anti-p38, anti-p-ERK, anti-ERK and anti-tubulin antibodies. The result is shown in FIG. 8.

Figure 8:
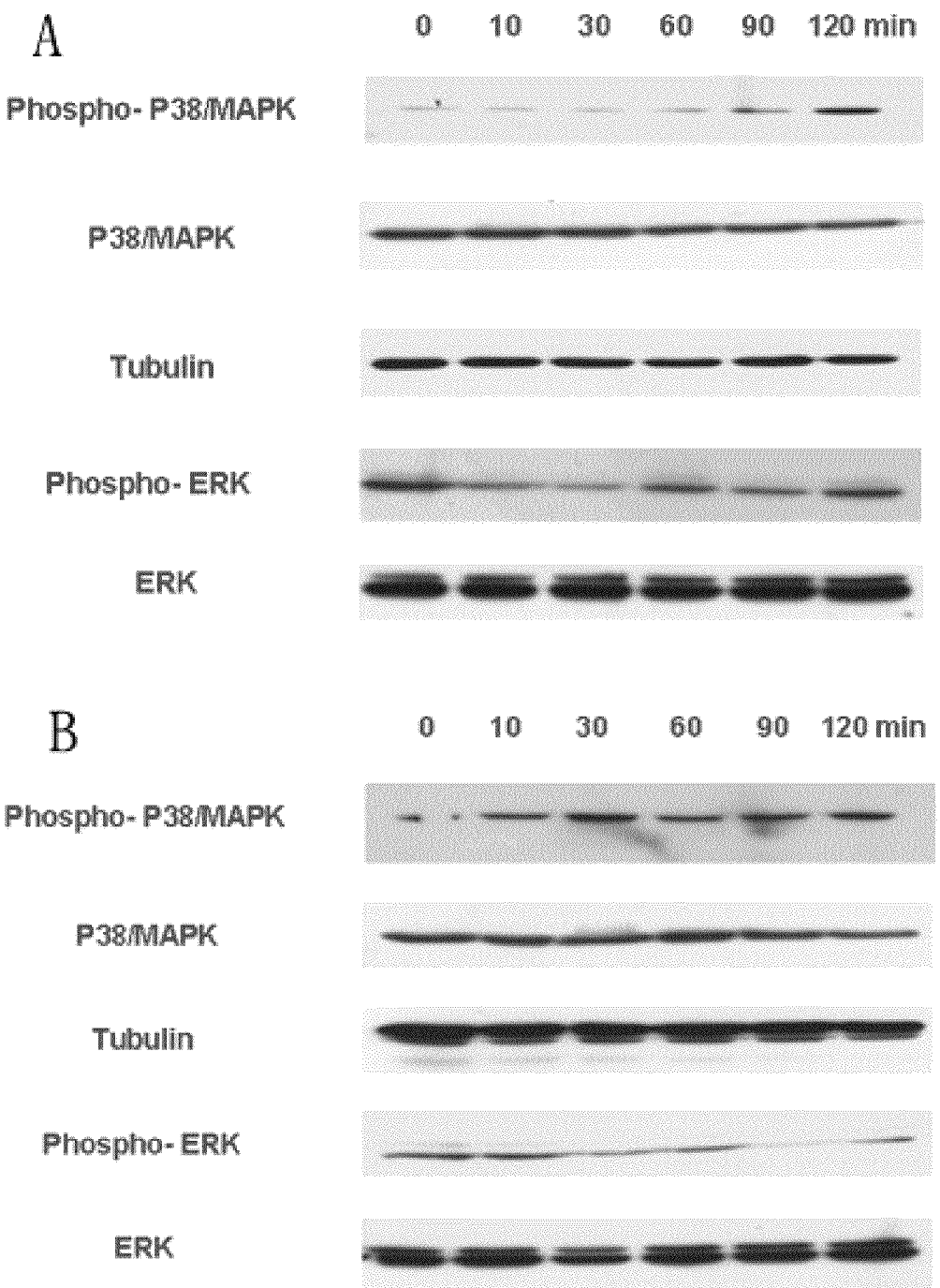
FIG. 8 shows a result of investigating the mechanism by which the GRS protein is involved in the apoptosis of cancer cells (A: treated with the GRS protein, B: treated with LPS)

As seen from FIG. 8, the GRS protein had an effect on the p38 kinase-related mechanism, known to be involved in cell growth or apoptosis.

Example 6

Effect of GRS Protein on Signaling Molecules

HeLa cells were cultured on a 6-well plate for 12 hours. After washing 2 times, the cells were allowed to stand in serum-starved DMEM for 3 hours. Then, the cells were cultured with GRS protein (150 nM) or TNF-α (15 ng/mL) for 10, 30, 60, 90 or 120 minutes, and then washed 2 times with cold phosphate buffer. The protein was extracted with 25 mM Tris-HCl (pH 7.4) lysis buffer containing 150 mM NaCl, 1 mM EDTA, 1 mM sodium orthovanadate, 20 mM sodium fluoride, 12 mM β-glycerophosphate, 10% glycerol, 1% Triton X-100 and protease inhibitor, separated by loading on 10% SDS-PAGE, and then transferred to polyvinylidene difluoride (PVDF) membrane (Millipore). Then, immunoblotting was performed using antibodies specific total MAPKs and phosphorylated MAPKs.

Figure 9:
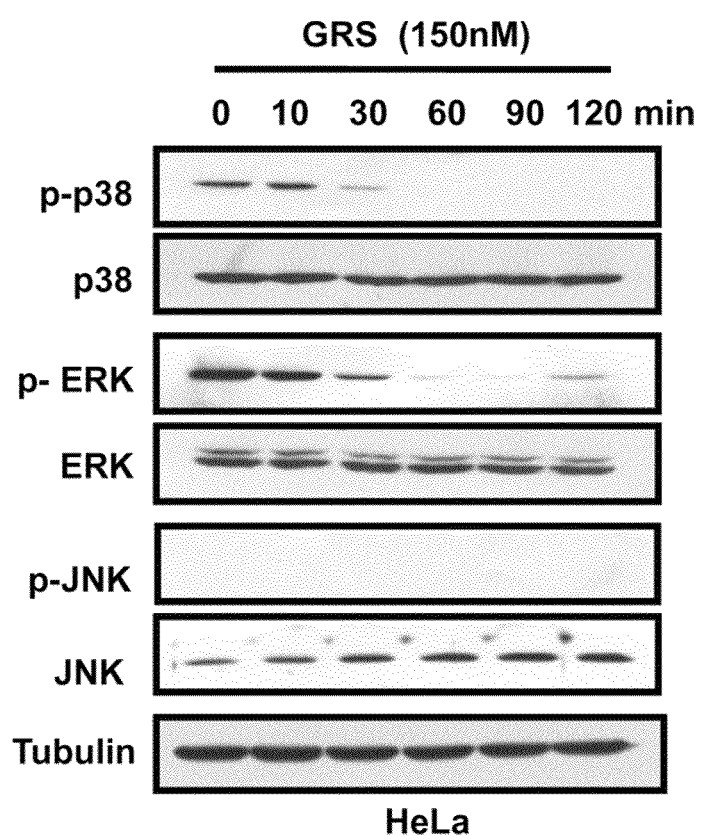
FIG. 9 shows a result of investigating the effect of the GRS protein on MAPKs through Western blotting.
Figure 10:
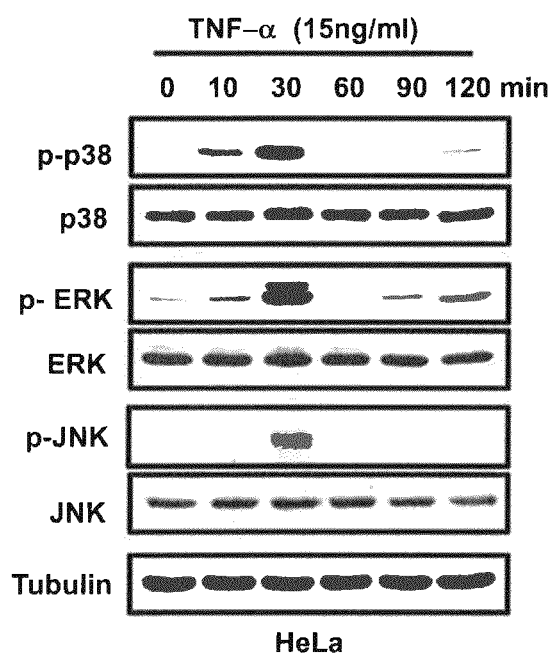
FIG. 10 shows a result of investigating the effect of TNF-α on MAPKs through Western blotting.
Figure 11:
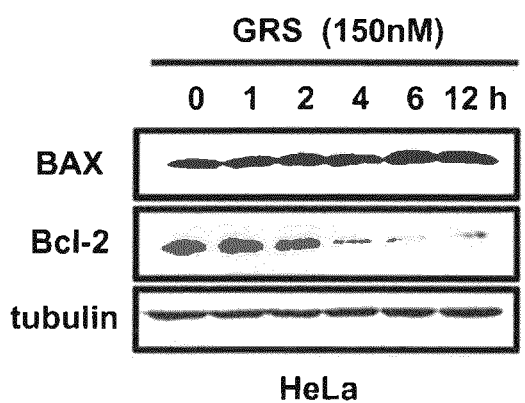
FIG. 11 shows a result of investigating the amount of Bax and Bcl-2 through Western blotting after treatment with the GRS protein.
Figure 12:
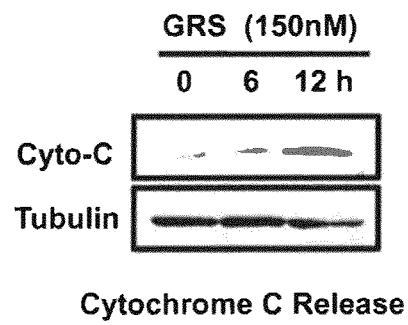
FIG. 12 shows a result of investigating the amount of cytochrome C through Western blotting after treatment with the GRS protein.

As seen from FIG. 9, the level of phosphorylated ERK and p38 MAPK increased with time after treatment with the GRS protein. In contrast, as seen from FIG. 10, phosphorylation of all the MAPKs increased in 30 minutes after treatment with TNF-α, suggesting that a different mechanism works. Also, in order to investigate whether the GRS-induced apoptosis is related with mitochondria, the intracellular level of Bax, Bcl-2 and cytochrome C was examined. First, HeLa cells were cultured with 150 nM GRS for a predetermined time. The cells were then collected, resuspended in 20 mM HEPES (pH 7.5) storage buffer containing 10 mM KCl, 1.5 mM $MgCl_2$, 0.5 mM EDTA, 1 mM DTT and protease inhibitor (Calbiochem), allowed to stand on ice for 5 minutes, and then homogenized for 6 cycles. Then, after centrifuging at 10,000 g for 10 minutes, protein was separated from the supernatant using 12% SDS-PAGE and transferred to PVDF membrane. Then, Western blotting was performed using cytochrome C or anti-tubulin antibody. As seen from FIG. 11, GRS did not affect the intracellular level of Bax, but resulted in reduction of the anti-apoptotic mediator Bcl-2. Also, as seen from FIG. 12, it increased the secretion of cytochrome C. To be concluded, GRS has pro-apoptotic activity in the HeLa cells.

Example 7

Identification of Cytokine Domain of GRS Protein

Figure 13:
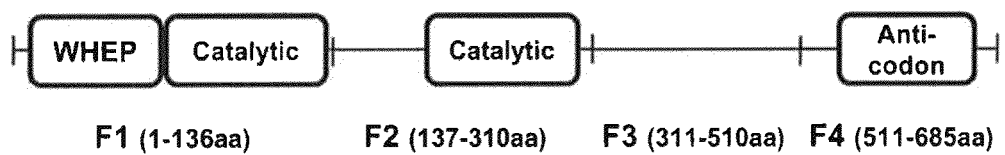
FIGS. 13 and 14 schematically show the full-length GRS protein and its fragments F1 to F4.
Figure 14:
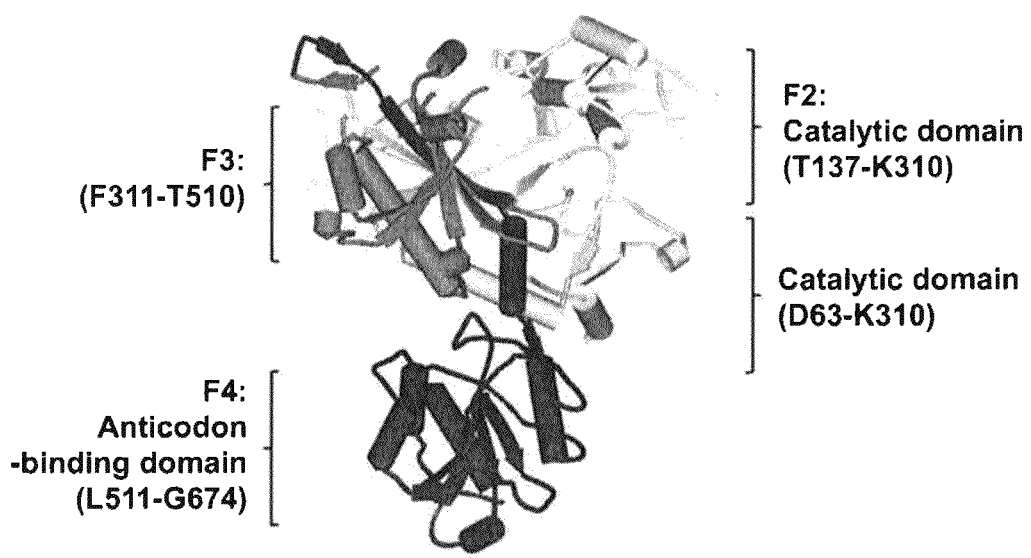
Figure 15:
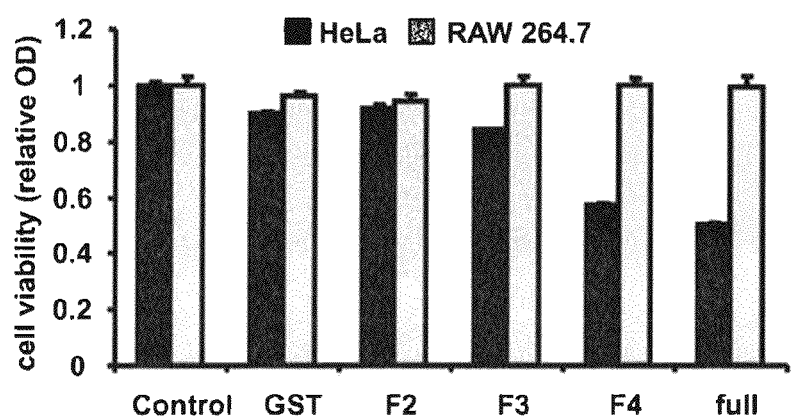
FIG. 15 shows cell viability for each fragment determined through MTT assay.

In order to investigate the domain of the GRS protein related to cytokine activity, four GRS fragments of SEQ ID NOs. 3 to 6 (FIGS. 13 and 14) were prepared and they were expressed with the GST fusion protein. After collecting three of the fragments except for the insoluble and unstable fragment F1, the GST-GRS fragments (F2 to F4) were purified and added to HeLa cells and RAW 264.7 cells. Then, cell viability was examined. As seen from FIG. 15, the fragment F4 including the C-terminal anticodon-binding domain exhibited pro-apoptotic cytokine activity.

INDUSTRIAL APPLICABILITY

Since the GRS proteins or fragments thereof have activity to induce apoptosis of cancer cell specifically, a composition comprising the GRS proteins or fragments thereof or a nucleic acid encoding thereof may be useful to treat cancer.

The invention claimed is:

1. A method for treating cancer comprising a step of administering to a subject in need thereof a pro-apoptotically effective amount of a polypeptide consisting of the amino acid sequence set forth in SEQ ID NO: 6.

2. The method of claim 1, wherein the cancer is selected from the group consisting of breast cancer, colorectal cancer, lung cancer, small cell lung cancer, stomach cancer, liver cancer, leukemia, bone cancer, pancreatic cancer, skin cancer, head or neck cancer, malignant melanoma, ocular cancer, uterine cancer, ovarian cancer, rectal cancer, anal cancer, colon cancer, fallopian tube cancer, endometrial carcinoma, cervical cancer, vaginal cancer, vulval cancer, Hodgkin's disease, esophageal cancer, small intestinal cancer, endocrine glandular cancer, thyroid cancer, parathyroid cancer, adrenal cancer, soft tissue sarcoma, urethral cancer, testicular cancer, prostate cancer, acute or chronic leukemia, lymphocytic lymphoma, bladder cancer, kidney or ureter cancer, kidney cell cancer, renal pelvic cancer, CNS tumor, primary CNS lymphoma, spinal cord tumor, brain-stem glioma, and pituitary adenoma.

* * * * *